(12) United States Patent
Hague et al.

(10) Patent No.: US 7,357,902 B2
(45) Date of Patent: Apr. 15, 2008

(54) PROCESS FOR THE REMOVAL OF OXYGEN FROM OLEFIN-CONTAINING PROCESS STREAMS

(75) Inventors: Matthew Hague, London (GB); Ian Raymond Little, West Lothian (GB); Warren John Smith, East Riding (GB)

(73) Assignee: Ineos Europe Limited, Hampshire (GB)

( * ) Notice: Subject to any disclaimer, the term of this patent is extended or adjusted under 35 U.S.C. 154(b) by 420 days.

(21) Appl. No.: 10/530,716

(22) PCT Filed: Sep. 23, 2003

(86) PCT No.: PCT/GB03/04052

§ 371 (c)(1),
(2), (4) Date: Apr. 8, 2005

(87) PCT Pub. No.: WO2004/033598

PCT Pub. Date: Apr. 22, 2004

(65) Prior Publication Data

US 2005/0281725 A1    Dec. 22, 2005

(30) Foreign Application Priority Data

Oct. 8, 2002    (GB) ................. 0223300.5

(51) Int. Cl.
*C07C 7/00* (2006.01)
*C07C 7/148* (2006.01)

(52) U.S. Cl. ............... 423/219; 423/245.3; 423/247; 423/248; 585/800; 585/845; 585/850; 585/855

(58) Field of Classification Search ........... 423/219, 423/247, 248, 245.3; 585/800, 845, 850, 585/855
See application file for complete search history.

(56) References Cited

U.S. PATENT DOCUMENTS 1,911,780 A * 5/1933 White et al. ............... 423/248
2,351,167 A * 6/1944 Ware ........................ 585/809
2,849,515 A * 8/1958 Leatherman et al. ........ 562/421
3,305,597 A * 2/1967 Straschil et al. ............ 585/259
3,549,719 A * 12/1970 Duyverman et al. ........ 423/219
4,105,588 A * 8/1978 Balducci et al. ............. 502/60
4,299,800 A    11/1981 Nishikawa et al.
4,734,273 A * 3/1988 Haskell ........................ 95/95
5,907,076 A * 5/1999 Ou et al. ..................... 585/800
6,132,694 A    10/2000 Wood et al.
6,204,218 B1    3/2001 Flick et al.
6,245,220 B1    6/2001 Didillon et al.

FOREIGN PATENT DOCUMENTS

GB    565991    12/1944

OTHER PUBLICATIONS

Dong, G., et al; "A novel catalyst for CO oxidation at low temperature"; *Catalysis Letters*, vol. 58, pp. 37-41 (1999).
Gardner, S.D., et al; "Catalytic Behavior of Nobel Metal/Reducible Oxide Materials for Low-Temperature CO Oxidation. I. Comparison of Catalyst Performance"; *Langmuir*; vol. 7; pp. 2135-2139 (1991).
Mergler, Y.J., et al; Comparison of Pt/MnO$_x$/SiO$_2$ and Pt/CoO$_x$/SiO$_2$ Catalysts for the CO Oxidation with O$_2$ and the no Reduction with CO; *Studies in Surface Science and Catalysis*, vol. 96; pp. 163-172 (1995).

* cited by examiner

*Primary Examiner*—Timothy C. Vanoy
(74) *Attorney, Agent, or Firm*—Nixon & Vanderhye

(57) ABSTRACT

Process for the removal of oxygen from a gas mixture comprising oxygen, at least one olefin, hydrogen, carbon monoxide and optionally at least one alkyne, the ratio of oxygen:hydrogen in the gas mixture being 1 part by volume of oxygen to at least 5 parts by volume of hydrogen. The process comprises contacting the gas mixture with a catalyst in a reaction zone under conditions sufficient to oxidise at least a portion of the hydrogen and to oxidize at least a portion of the carbon monoxide and without significant hydrogenation of the at least one olefin. The catalyst comprises at least one metal or oxide of a metal from the $10^{th}$ group of the Periodic Table of Elements, the metal or oxide of the metal being supported on an oxide support, provided that the catalyst also comprises tin.

20 Claims, No Drawings

PROCESS FOR THE REMOVAL OF OXYGEN FROM OLEFIN-CONTAINING PROCESS STREAMS

This application is the U.S. National Phase of International Application PCT/GB03/004052, filed 23 Sep. 2003, which designated the U.S. PCT/GB03/004052 claims priority to British Application No. 0223300.5 filed 8 Oct. 2002. The entire content of these applications are incorporated herein by reference.

The present invention relates to a process for the removal of oxygen from gas mixtures comprising oxygen, olefin, hydrogen and carbon monoxide and, in particular, to a process for the removal of oxygen from such gas mixtures by the selective oxidation of both hydrogen and carbon monoxide without incurring significant hydrogenation of the olefin.

Gas mixtures comprising oxygen, olefins such as ethylene and/or propylene, hydrogen and carbon monoxide may be produced by a variety of industrial chemical processes including the steam cracking of hydrocarbons, the dehydrogenation of paraffinic feedstocks, the conversion of methanol to olefins and the auto-thermal cracking of hydrocarbons.

Typically, in an auto-thermal cracking process, a paraffinic hydrocarbon such as ethane is mixed with an oxygen-containing gas and the mixture subsequently contacted with a catalyst such as a palladium or platinum based catalyst. In the process the paraffinic hydrocarbon is partially combusted, and the heat produced by the combustion reaction is used to drive a dehydrogenation reaction. The product stream from the auto-thermal cracking process typically comprises olefins such as ethylene, oxygen, unconverted paraffinic hydrocarbon, hydrogen, carbon monoxide, carbon dioxide and water. The product stream may also comprise low levels of alkynes, dienes, aromatic compounds, and oxygenated compounds such as aldehydes, organic acids and ethers. The auto-thermal cracking of paraffinic hydrocarbons is described, for example, in EP-A-0 332 289.

It is known that the presence of oxygen in industrial process streams can act as a contaminant and/or poison in certain downstream processes. For example, oxygen may contaminate fuel gas streams derived from demethanisers. In addition, oxygen can also cause or contribute to fouling of downstream processing equipment, particularly compressors. Minimising this fouling may help to prolong the lifetime of the processing equipment and also reduce the frequency of equipment shut-downs.

It is also known that the presence of alkynes, such as acetylene, in olefin-containing process streams is detrimental to certain downstream processes. For example, where the olefin-containing process stream is to be used in the manufacture of polyethylene, the presence of alkyne in the olefin process stream is undesirable in that it can affect the quality of the polyethylene product.

It is known to remove oxygen from olefin-containing gas mixtures by absorption using, for example, copper-based solid state beds. Typically, these copper based absorption beds comprise metallic copper dispersed on a solid support such as a metal and/or non-metal oxide and are generally operated at relatively low temperatures, for example 20° to 30° C. However, such beds are generally capable of removing only low levels (less than 10 ppm) of oxygen. In addition, if alkyne, such as acetylene, is present in the gas mixture, it tends to react with the copper, forming, for example, copper acetylide and thereby poisoning the bed.

U.S. Pat. No. 6,069,288 relates to a process for selectively separating hydrogen or both hydrogen and carbon monoxide from hydrocarbons containing reactive unsaturated hydrocarbons. The process involves catalytically reacting hydrogen and oxygen to eliminate the majority of the hydrogen, and then reacting the remaining low-level hydrogen with the reactive unsaturated hydrocarbons. Suitable catalysts can be prepared by distributing metal(s) and/or metal oxide(s) selected from the elements of Groups IB through VIIB and Group VIII on inert supports.

U.S. Pat. No. 6,204,218 relates to a catalyst for removing alkynes, dienes, monounsaturated hydrocarbons and/or oxygen by hydrogenation from reaction feed streams or product streams which contain sulphur, arsenic and/or antimony catalyst poisons. The catalyst comprises at least one of nickel, palladium and platinum and at least one of copper, silver and gold supported on silica.

In view of the above, it would be desirable to remove oxygen from olefin-containing process streams such as product streams from the auto-thermal cracking of hydrocarbons.

Where the olefin-containing process stream also comprises alklynes, such as acetylene, it would be desirable to remove both the oxygen and alkyne therefrom.

In particular, it would be highly desirable to remove oxygen and where present, alkyne, from the olefin-containing process stream without incurring significant loss of olefin.

Thus, there remains a need for a process for the removal of oxygen from olefin-containing gas mixtures which optionally also contain alkynes and wherein there is no significant loss of olefin Thus, according to the present invention there is provided a process for the removal of oxygen from a gas mixture comprising oxygen, at least one olefin, hydrogen, carbon monoxide and optionally at least one alkyne, the ratio of oxygen:hydrogen in the gas mixture being at least 1 part by volume of oxygen to at least 5 parts by volume of hydrogen, which process comprises contacting the gas mixture with a catalyst in a reaction zone under conditions sufficient to oxidise at least a portion of the hydrogen and to oxidise at least a portion of the carbon monoxide and without significant hydrogenation of the at least one olefin, wherein the catalyst comprises at least one metal or oxide of a metal selected from the group consisting of the $10^{th}$ group and the $11^{th}$ group of the Periodic Table of Elements, the metal or oxide of the metal being supported on an oxide support, provided that where the catalyst comprises at least one metal or oxide of a metal from the $10^{th}$ group of the Periodic Table of Elements supported on an oxide support, the catalyst also comprises tin and provided that where the catalyst comprises at least one metal or oxide of a metal of the $11^{th}$ group of the Periodic Table of Elements the oxide support is a zeolite.

Advantageously, the process of the present invention enables oxygen to be removed from olefin-containing gas mixtures which contain low levels, such as 2000 ppm or less of oxygen and which typically contain 1000 ppm or less of oxygen. (In this specification "ppm" means parts per million by volume). Furthermore, oxygen can be removed from olefin-containing gas mixtures which have a low concentration of oxygen and a high concentration of hydrogen, for example, the gas mixture may comprise at least 10 vol % hydrogen optionally 20 vol % hydrogen or greater, for example, 40 vol % or greater. Where the olefin-containing gas mixture comprises alkynes, the process of the present invention enables both oxygen and alkyne to be removed therefrom. The removal of oxygen and optional alkyne may be achieved in the presence of high concentrations of hydrogen and without any significant loss of olefin. Typically, the gas mixture leaving the reaction zone after removal of oxygen and optionally alkyne contains at least 90% of the hydrogen present in the feed to the reaction zone. There may be at least 10 vol % hydrogen in the gas mixture leaving the reaction zone.

The olefin may be a $C_2$-$C_5$ olefin, for example, ethylene, propylene, n-butene, sec-butene, iso-butene, pentenes and mixtures thereof. Suitably, the olefin is ethylene, propylene or mixtures thereof.

Although, the process of the present invention may be used to remove oxygen from gas mixtures comprising a high proportion of olefin, such as 95 vol % olefin based on the total feed, the process of the present invention is particularly advantageous where the gas mixture comprises from greater than 0 and up to and including 75 vol % olefin, and preferably, greater than 0 and up to and including 60 vol % olefin.

The likelihood of undesirable hydrogenation reactions, such as the hydrogenation of olefin to alkane, tends to increase as the concentration of hydrogen in the gas mixture increases. Surprisingly, therefore, the process of the present invention enables oxygen to be removed from olefin-containing gas mixtures having high concentrations of hydrogen without incurring significant loss of olefin.

Thus, suitably, the gas mixture may comprise greater than 0 and up to and including 95 vol % hydrogen, based on the total feed, preferably, greater than 0 and up to and including 75 vol % hydrogen, for example, greater than 0 and up to and including 60 vol % hydrogen.

The ratio of oxygen to hydrogen, by volume, for use in the present invention is one part by volume of oxygen to at least 5 parts by volume of hydrogen (1:>5) Suitably, the ratio of oxygen to hydrogen, by volume, may be in the range 1:10 to 1:50,000, for example, in the range 1:20 to 1:100,000, such as, in the range, 1:50 to 1:50,000.

Suitably, the gas mixture may comprise oxygen in a concentration of from greater than 0 up to and including 10 vol % based on the total feed, such as from 0 up to and including 5 vol %, for example, from greater than 0 up to and including 2 vol % oxygen.

Suitably, the gas mixture comprises from greater than 0 up to and including 30 vol % carbon monoxide based on the total feed, such as from greater than 0 up to and including 20 vol % carbon monoxide, for example, from greater than 0 up to and including 15% carbon monoxide.

In addition to the olefin, oxygen, hydrogen and carbon monoxide, the gas mixture may also comprise one or more alkanes such as a $C_1$-$C_5$ alkane, for example, methane, ethane, propane, n-butane, sec-butane, iso-butane or mixtures thereof.

Suitably, the concentration of alkane based on the total feed is from greater than 0 up to and including 95 vol %, for example, from greater than 0 up to and including 60 vol %.

The gas mixture may also comprise low levels (such as less than 25 vol %) of each of one or more other hydrocarbon compounds, such as an alkyne, for example acetylene, methylacetylene, phenylacetylene, ethylacetylene or mixtures thereof, dienes, for example, butadiene, aromatic hydrocarbons, for example, benzene, toluene, ethylbenzene, styrene or mixtures thereof and oxygenated hydrocarbons, for example, aldehydes, organic acids, ethers, alcohols or mixtures thereof.

Where alkyne, e.g. acetylene, is present in the gas mixture, the concentration of alkyne, based on the total feed, is preferably from greater than 0 up to and including 20 vol %, more preferably, from greater than 0 up to and including 5 vol % and especially, from greater than 0 up to and including 1 vol %.

One or more other components, such as diluents, may also be present in the gas mixture. For example, the gas mixture may comprise a diluent such as nitrogen and/or compounds such as ammonia, water, carbon dioxide, alcohols, amines, esters and sulphur-containing compounds.

The catalyst employed in the process of the present invention comprises at least one metal or oxide of a metal selected from the group consisting of the $10^{th}$ group and $11^{th}$ group of the Periodic Table of Elements supported on an oxide support, provided that where the catalyst comprises at least one metal or oxide of a metal from the $10^{th}$ group of the Periodic Table of Elements supported on an oxide support, it also comprises tin and provided that where the catalyst comprises at least one metal or oxide of a metal of the $11^{th}$ group of Periodic Table of Elements, the oxide support is a zeolite.

The numbering of the groups of the Periodic Table of Elements used in this specification follows the current numbering recommended by the International Union for Pure and Applied Chemistry (IUPAC). For the avoidance of doubt, the $10^{th}$ group consists of the elements, nickel, palladium and platinum and the $11^{th}$ group consists of the elements copper, silver and gold.

Where the catalyst comprises at least one metal or oxide of a metal from the $11^{th}$ group of the Periodic Table of Elements, the catalyst comprises at least 0.01 wt %, based on the total weight of the dry catalyst, of the at least one metal or oxide of a metal.

Preferably, where the catalyst comprises at least one metal or oxide of a metal from the $11^{th}$ group of the Periodic Table of Elements, the metal is copper.

Where the catalyst comprises copper or an oxide of copper, the copper is present in an amount in the range 1-15 wt % based on the total weight of the dry catalyst and preferably, in the range 5-10 wt %.

Where the catalyst comprises at least one metal or oxide of a metal from the $10^{th}$ group of the Periodic Table of Elements, the catalyst comprises at least 0.01 wt %, based on the total weight of the dry catalyst, of the at least one metal or oxide of a metal.

Preferably, where the catalyst comprises at least one metal or oxide of a metal from the $10^{th}$ group of the Periodic Table of Elements, the metal is chosen from platinum or palladium, and more preferably, platinum.

Where the catalyst comprises platinum or an oxide of platinum, the platinum is suitably present in an amount in the range 0.01-15 wt % based on the total weight of the dry catalyst, preferably, in the range 0.1-5 wt %.

Where the catalyst comprises at least one metal or oxide of a metal from the $10^{th}$ group of the Periodic Table of Elements, the catalyst also comprises tin.

The tin may be present in the catalyst in an amount in the range 0.01-60 wt % based on the total dry weight of the catalyst, preferably, in the range 0.1-20 wt %, such as in the range 0.1-15 wt %, for example, 10 wt %.

The weight ratio of the metal of the $10^{th}$ group to tin is suitably 99-1:1-99.

Where the metal of the $10^{th}$ group is platinum, the weight ratio of platinum to tin is 99-1:1-99, preferably, in the range 1:1 to 1:50, such as in the range 1:1 to 1:10, for example, in the range 1:1 to 1:5.

Where the catalyst comprises at least one metal or oxide of a metal from the $10^{th}$ group of the Periodic Table of Elements and tin, the catalyst may also comprise one or more metals or oxides of metals selected from the group consisting of the transition series and the lanthanide series of the Periodic Table of Elements excluding tin and metal(s) or oxides of metal(s) from the $10^{th}$ group of the Periodic Table.

Suitably, the transition metal may be selected from titanium, zirconium, manganese, cobalt, iron or mixtures thereof.

Suitably, the transition metal oxides may be selected from oxides of titanium, zirconium, manganese, cobalt, iron and mixtures thereof.

Suitably, the metal or oxide of metal from the lanthanide series of the Periodic Table may be cerium.

The oxide support may be any suitable oxide support. Typically, the oxide support will be an inert porous support. Suitable inert porous supports include silica, alumina, zirconia, clay, zeolites and MCM, preferably zeolites.

Suitable zeolites include zeolite A, zeolite X, zeolite Y, high silica zeolites such as ZSM-5 and silicalite.

Where the catalyst comprises a metal from the $11^{th}$ group, such as copper, the oxide support is preferably, zeolite A or zeolite X, especially zeolite A.

Where the catalyst comprises a metal from the $10^{th}$ group, such as platinum, the oxide support is preferably, alumina or silica, especially silica.

Preferably, the catalyst employed in the process of the present invention is copper supported on a zeolite, especially copper supported on zeolite A or platinum and tin supported on silica.

The catalyst employed in the process of the present invention may be prepared by any suitable technique known in the art, for example, ion exchange, impregnation, vapour deposition and dispersion. Suitable catalysts may be obtained for example from STC Catalysts Inc., Johnson Matthey & Englehard.

Preferably, where the catalyst comprises a metal of the $11^{th}$ group, such as copper, the catalyst is prepared by ion-exchange. Where the catalyst comprises a metal from the $10^{th}$ group, such as platinum, the catalyst is most suitably prepared by impregnation.

The process of the present invention is carried out under conditions whereby at least a portion of the hydrogen present in the gas mixture is oxidised to form water and at least a portion of the carbon monoxide present in the gas mixture is oxidised to form carbon dioxide.

Suitably, the process is carried out at a temperature in the range 50-300° C., such as in the range 100-250° C.

Suitably, the process of the present invention is carried out at a total pressure in the range 1-80 bara (bar absolute), more typically 1-50 bara, such as in the range 1-30 bara. Total pressure in the range 1-10 or more narrowly 1:5 bara may be used. However, it has been found to be advantageous to carry out the process at a total pressure of at least 10 bara, preferably 15-35 bara.

The gas mixture is contacted with the catalyst at a gas hourly space velocity (GHSV) in the range 100-100,000 $h^{-1}$, preferably, within the range 1000-50,000 $h^{-1}$. It will be understood however, that the optimum gas hourly space velocity is dependent upon both the pressure employed and the nature of the composition of the gas mixture.

The extent to which oxygen is removed from the gas mixture will depend upon the exact reaction conditions employed and the initial concentration of oxygen present in the gas mixture. Typically, in the process of the present invention, the concentration of oxygen may be reduced from at least 1000 ppm to levels below 10 ppm, such as below 1 ppm and may even be reduced to essentially minimal levels, such as less than 0.1 ppm.

Where alkyne is present in the gas mixture, the concentration of alkyne can be reduced to essentially minimal levels. Typically, where the catalyst comprises copper, the concentration of alkyne may be reduced to less than 20 ppm.

The reaction products of the process of the present invention include water and carbon dioxide. Such reaction products can be readily separated from the olefinic hydrocarbons using any suitable technique, such as drying and washing with caustic solution.

The process of the present invention is particularly useful when the olefin-containing gas mixture is obtained, at least in part, from the auto-thermal cracking of hydrocarbons.

Accordingly, the present invention provides a process for the removal of oxygen from a gas mixture comprising oxygen, at least one olefin, hydrogen, carbon monoxide and optionally at least one alkyne, which process comprises the steps: (a) contacting at least one hydrocarbon with a molecular oxygen-containing gas in a first reaction zone with a catalyst capable of supporting combustion beyond the normal fuel-rich limit of flammability and wherein the stoichiometric ratio of hydrocarbon to oxygen is 5 to 16 times the stoichiometric ratio of hydrocarbon to molecular oxygen-containing gas for complete combustion to carbon dioxide and water, to produce a product stream comprising oxygen, at least one olefin, hydrogen, carbon monoxide and optionally at least one alkyne,(b) contacting in a second reaction zone, at least a portion of the product stream from step (a) having a ratio of oxygen to hydrogen of at least one part by volume of oxygen to at least 5 parts by volume of hydrogen with a catalyst under conditions sufficient to oxidise at least a portion of the hydrogen and to oxidise at least a portion of the carbon monoxide and without significant hydrogenation of the at least one olefin, wherein the catalyst comprises at least one metal or oxide of a metal selected from the group consisting of the $10^{th}$ group and the $11^{th}$ group of the Periodic Table of Elements the metal or oxide of the metal being supported on an oxide support, provided that where the catalyst comprises at least one metal or oxide of a metal from the $10^{th}$ group of the Periodic Table of Elements supported on an oxide support the catalyst also comprises tin, and provided that where the catalyst comprises at least one metal or oxide of a metal selected from the $11^{th}$ group of Periodic Table of the Elements the oxide support is a zeolite.

In step (a) the hydrocarbon may be a liquid or gaseous hydrocarbon. Suitable liquid hydrocarbons include naphtha, gas oils, vacuum gas oils and mixtures thereof. Preferably, however, gaseous hydrocarbons such as ethane, propane, butane and mixtures thereof are employed. Suitably, the hydrocarbon is a paraffin-containing feed comprising hydrocarbons having at least two carbon atoms.

The hydrocarbon feed is mixed with any suitable molecular oxygen-containing gas. Suitably, the molecular oxygen-containing gas is molecular oxygen, air, and/or mixtures thereof. The molecular oxygen-containing gas may be mixed with an inert gas such as-nitrogen, helium or argon.

Additional feed components may be included, if so desired. Suitably, methane, hydrogen, carbon monoxide, carbon dioxide or steam may be co-fed into the reactant stream.

The stoichiometric ratio of hydrocarbon to molecular oxygen-containing gas is 5 to 16, preferably, 5 to 13.5 times, preferably, 6 to 10 times the stoichiometric ratio of hydrocarbon to oxygen-containing gas required for complete combustion of the hydrocarbon to carbon dioxide and water.

The hydrocarbon may be passed over the catalyst in the first reaction zone at a gas hourly space velocity of greater than 10,000 h$^{-1}$, preferably above 20,000 h$^{-1}$ and most preferably, greater than 100,000 h$^{-1}$. It will be understood, however, that the optimum gas hourly space velocity will depend upon the pressure and nature of the feed composition.

Preferably, hydrogen is co-fed with the hydrocarbon and molecular oxygen-containing gas into the first reaction zone. The molar ratio of hydrogen to molecular oxygen-containing gas can vary over any operable range provided that the desired olefin product is produced. Suitably, the molar ratio of hydrogen to molecular oxygen-containing gas is in the range 0.2 to 4, preferably, in the range 1 to 3.

Preferably, the reactant mixture of hydrocarbon and molecular oxygen-containing gas (and optionally hydrogen co-feed) is preheated prior to contact with the catalyst in the first reaction zone. Generally, the reactant mixture is preheated to temperatures below the autoignition temperature of the reactant mixture.

The catalyst in the first reaction zone may be any catalyst capable of supporting combustion beyond the fuel rich limit of flammability. Any suitable catalyst known in the art may be employed. Typically, the catalyst will comprise a Group 8, 9, or 10 metal such as platinum, palladium, ruthenium, rhodium, osmium and iridium and, in particular platinum and/or palladium. Typical Group 8, 9 or 10 metal loadings range from 0.01 to 100 wt %, preferably, between 0.01 to 20 wt %, and more preferably, from 0.01 to 10 wt % based on the total dry weight of the catalyst.

The catalyst may be promoted with one or more suitable promoters. Where a Group 8, 9 or 10 catalyst is employed, it is preferably promoted with a Group 13, 14, and/or 15 metal. Alternatively, the promoter may be a transition metal; the transition metal promoter being a different metal to that which may be employed as the Group 8, 9 or 10 transition metal catalytic component. Examples of catalysts suitable for use in the auto-thermal cracking process include Pt/Ga, Pt/In, Pt/Sn, Pt/Ge, Pt/Cu, Pd/Sn, Pd/Ge, Pd/Cu and Rh/Sn. The atomic ratio of Rh, Pt or Pd to the Group 13, 14 or transition metal promoter may be 1:0.1-50.0.

Preferably, catalyst in the first reaction zone is supported. Any suitable support may be used such as ceramic or metal supports, but ceramic supports are generally preferred. Suitable ceramic supports include corderite, lithium aluminium silicate (LAS), alumina ($\alpha$-Al$_2$O$_3$), yttria stabilised zirconia, alumina titanate, niascon, and calcium zirconyl phosphate. The ceramic supports may be wash-coated, for example, with $\gamma$-Al$_2$O$_3$.

The catalyst exit temperature in the first reaction zone may suitably be in the range 600° C. to 1200° C., preferably, in the range 850° C. to 1050° C. and, most preferably, in the range 900° C. to 1000° C.

The auto-thermal cracking process in the first reaction zone may be carried out at atmospheric or elevated pressure. Suitably, the pressure may be in the range from 0 to 2 bara, preferably 1.5 to 2 bara, for example 1.8 bara. Elevated pressures of, for example, 2 to 50 bara, may also be suitable.

Typically, the product of the auto-thermal cracking process of step (a) comprises a mixture of olefins such as ethylene, propylene and the butenes, oxygen, carbon monoxide, carbon dioxide and water. The product stream may further comprise alkanes such as methane, ethane, propane, the butanes and mixtures thereof and alkynes such as acetylene, methylacetylene, phenylacetylene, ethylacetylene and mixtures thereof.

Suitably, the product stream from step (a) comprises 0.0001-1 vol % oxygen, 10-60 vol % hydrogen, 1-10 vol % carbon monoxide and 10-60 vol % olefin.

Alternatively, the product stream from step (a) may suitably comprise 0.0001-1 vol % oxygen, 10-60 vol % hydrogen, 1-10 vol % carbon monoxide, 10-60 vol % olefin and 0.01-2 vol % alkyne.

At least a portion of the product stream produced in the auto-thermal cracking process of step (a) may be passed directly or indirectly and as one or more feed streams to the second reaction zone.

The present invention will now be illustrated by way of example only and with reference to the following examples.

Preparation of Catalyst A

A copper-exchanged zeolite A catalyst was prepared by ion exchange as follows:

Zeolite 3A extrudates (1.6 mm, obtained from Aldrich Chemical Co.) were crushed and sieved to obtain a 0.5-0.85 mm fraction 0.30 ml of the 0.5-0.85 mm fraction was added at room temperature to a vessel containing 500 ml of a 0.05 molar solution of copper (II) nitrate in deionised water. The vessel was then sealed and the mixture allowed to stand under ambient conditions overnight with occasional agitation. After decanting the supernatant solution from the vessel, 500 ml of fresh 0.05M Cu(NO$_3$)$_2$ was added to the vessel. The vessel was again allowed to stand overnight with occasional agitation under ambient conditions. After decanting the supernatant solution, the solid remaining in the vessel was washed with four aliquots (25 ml each) of deionised water. The solid was then transferred to a Buchner filter funnel to remove excess solution and dried in an oven under a nitrogen atmosphere at 130° C. for three hours.

Analysis by X-ray fluorescence showed that the copper-exchanged zeolite A catalyst contained 7.0% copper by weight based on the total weight of dry catalyst.

Preparation of Catalyst B

Preparation as for catalyst A was repeated except that Zeolite 13X beads (4-8 mesh, obtained from Aldrich Chemical Co.) were used in place of Zeolite A extrudates.

X-ray fluorescence analysis showed that the copper-exchanged zeolite X catalyst contained 7.7% copper by weight based on the total weight of dry catalyst.

Preparation of Catalyst C

A platinum and tin catalyst supported on silica was prepared by impregnation as follows:

5 g of a 1% w/wPt-silica material (ex Engelhard) were placed in 10 ml deionised water. 1 g of 30 mesh reagent grade tin granules were added. The water was boiled for 3 minutes, cooled to room temperature and nitric acid added to give a 2.25 molar solution. The mixture was slowly stirred and heated to 50° C. The tin granules dissolved and a white suspension then settled out. The temperature was increased to 110° C. and held at this temperature for 16 h to obtain a dry solid. The solid was sieved to remove particles smaller than 0.5 mm.

Preparation of Catalyst D

Preparation as for catalyst C was repeated except that 0.5 g of tin granules were used.

Elemental analysis of the catalyst gave 0.7% w/w Pt and 2.61% w/w Sn.

Preparation of Catalyst E

Preparation as for catalyst C was repeated except that 0.125 g of tin granules were used. Elemental analysis of the catalyst gave 0.73% w/w Pt and 1.87% w/w Sn.

Preparation of Comparative Catalyst F

A platinum containing solution was prepared by mixing 0.77 g of $Pt(NH_3)_4OH_2 \cdot H_2O$ with 60 ml of deionised water followed by drop-wise addition of nitric acid until the platinum salt fully dissolved. To this was added 50.2 g of crushed and sieved GS57 silica (0.5-2 mm sized granules) and this mixture was dried at 110° C. with occasional mixing over a period of 6 hours. The impregnated support was calcined at 250° C. for 1 hour. This group 10 metal catalyst did not contain tin.

Preparation of Catalyst G 1.08 g of tin wire was added to 20 ml of water and 10 ml of nitric acid. The mixture was vigorously stirred until the wire dissolved and a white suspension had formed. This suspension was then added to 18.0 g of Comparative Catalyst F, which was subsequently dried at 110° C. for 16 hours. The impregnated support was calcined at 250° C. for 1 hour, followed by sieving to remove particles smaller than 0.5 mm.

EXAMPLE 1

A 2 ml sample of Catalyst A (copper exchanged Zeolite A) was loaded into a tube-reactor with internal diameter 10 mm such that the catalyst lay close to the middle of the reactor and was surrounded on either side by inert pre-heat material (fused alumina).

The catalyst was activated by heating the reactor under a stream of dry nitrogen (250 ml $min^{-1}$) at atmospheric pressure to 140° C. at 1° C. $min^{-1}$. Hydrogen gas was then introduced into the reactor at a level of 5 mol-% and was increased incrementally up to 100 mol-%, while the nitrogen flow was gradually reduced to zero over a period of 30 minutes. After holding at 140° C. under pure hydrogen gas (250 ml $min^{-1}$) for one hour, the temperature was ramped at 1° C. $min^{-1}$ to 200° C. and was held there under pure hydrogen flow for 15 hours. The reactor was then pressurised to 1 barg (bar gauge) under hydrogen.

Subsequent to pressurisation of the reactor, a gas mixture comprising 0.05 mol % oxygen, 0.2 mol % acetylene, 42 mol % hydrogen, 6 mol % carbon monoxide, 24 mol % ethylene, 1.5 mol % water was passed through the catalyst bed at 200° C., 1 barg and a gas hourly space velocity (GHSV) of 5,000 litres $h^{-1}$.

The composition of the gaseous mixture exiting the catalyst bed was analysed. The hydrocarbon concentration was analysed by gas chromatography and the oxygen concentration was analysed using an oxygen meter manufactured by Teledyne Analytical Instruments Inc. The results are given in Table 1 below.

EXAMPLES 2 AND 3

Example 1 was repeated except for the following differences:

In Example 2 the temperature was held at 140° C. under pure hydrogen for 40 minutes and the gas mixture comprised 0.05 mol % oxygen, 0.2 mol % acetylene, 42 mol % hydrogen, 6 mol %. carbon monoxide and 24 mol % ethylene.

In Example 3 the temperature was held at 140° C. under pure hydrogen for 35 minutes and the reactor was pressurised to 2.5 barg under dry nitrogen. The results for each of Examples 24 are given in Table 1 below.

COMPARATIVE EXAMPLES 1-3

Each of Examples 1-3 was repeated except that no catalyst was used. The results are given in Table 1 below.

EXAMPLE 4

A 2 ml sample of Catalyst B (copper-exchanged zeolite X) was loaded into a tube-reactor with internal diameter 10 mm such that the catalyst lay close to the middle of the reactor, and was surrounded on either side by inert pre-heat material (fused alumina).

The catalyst was activated by heating the reactor under a stream of dry nitrogen (250 ml $min^{-1}$) at atmospheric pressure to 140° C. at 1° C. $min^{-1}$. After 50 minutes at 140° C., hydrogen gas was introduced at a level of 5 mol % and was increased incrementally up to 100 mol-%, while the nitrogen flow was gradually reduced to zero over a period of 30 minutes. After holding at 140° C. under pure hydrogen gas (250 ml $min^{-1}$) for 25 minutes, the temperature was ramped at 1° C. $min^{-1}$ to 200° C. and was held there under pure hydrogen flow for 15 hours. The reactor was then pressurised to 1 barg under dry nitrogen.

Subsequent to pressurising the reactor, a gas mixture comprising 0.05 mol % oxygen, 0.2 mol % acetylene, 42 mol % hydrogen, 6 mol % carbon monoxide, 24 mol % ethylene, 1.5 mol % water was passed through the catalyst bed at 200° C., 1 barg and a gas hourly space velocity (GHSV) of 5,000 $h^{-1}$ The composition of the gas exiting the catalyst bed was analysed. The hydrocarbon concentration was analysed by gas chromatography and the oxygen concentration was analysed using an oxygen meter manufactured by Teledyne Analytical Instruments Inc. The results are given in Table 1 below.

COMPARATIVE EXAMPLE 4

Example 4 was repeated except that no catalyst was used. The results are given in Table 1 below.

TABLE 1

| | | Initial Gas Composition | | | Exit Gas Composition | | |
|---|---|---|---|---|---|---|---|
| | Catalyst | Oxygen mol % | Acetylene mol % | Ethylene mol % | Oxygen ppm | Acetylene mol % | Ethane mol % |
| Example 1 | A | 0.05 | 0.2 | 24 | <0.1 | <0.002 | 0.019 |
| Comparative 1 | — | 0.05 | 0.2 | 24 | 1000 | 0.2 | 0.012 |
| Example 2 | A | 0.05 | 0.2 | 24 | <0.1 | <0.002 | 0.018 |
| Comparative 2 | — | 0.05 | 0.2 | 24 | 1000 | 0.2 | 0.012 |
| Example 3 | A | 0.05 | 0.2 | 24 | <0.1 | <0.002 | 0.041 |
| Comparative 3 | — | 0.05 | 0.2 | 24 | 1000 | 0.2 | 0.014 |

TABLE 1-continued

| | Catalyst | Initial Gas Composition | | | Exit Gas Composition | | |
| --- | --- | --- | --- | --- | --- | --- | --- |
| | | Oxygen mol % | Acetylene mol % | Ethylene mol % | Oxygen ppm | Acetylene mol % | Ethane mol % |
| Example 4 | B | 0.05 | 0.2 | 24 | 0.1 | 0.002 | 0.04 |
| Comparative 4 | — | 0.05 | 0.2 | 24 | 1000 | 0.2 | 0.011 |

As can be seen from Table 1 the process of the present invention removes essentially all of the oxygen initially present in the gas mixture without incurring significant loss of olefin (little ethane having been detected).

Where acetylene is present in the gas mixture, the process of the present invention enables the concentration of acetylene to be reduced to essentially minimal levels without significant loss of olefin.

General Experimental Procedure 1

A 1 ml sample of catalyst was loaded into a stainless steel tubular reactor (10 mm internal diameter) supported downstream by a glass wool plug. A nitrogen stream was passed over the catalyst to purge the system of air, the reactor heated by an external furnace to the required experimental temperature, and the nitrogen pressure raised to 2.0 barg. An initial gas feed comprising, by volume, 0.07% oxygen, 33.5% hydrogen, 7% carbon monoxide, 28.7% ethylene, 0.21% acetylene and nitrogen as balance was passed through a deionised water bubbler at 20° C. prior to admission to the reactor. The nitrogen flow through the reactor was replaced by the gas feed at 2.0 barg and flow rate to give 10,000 GHSV. Subsequent temperature changes were made in the presence of the gas feed. The composition of the gas exiting the catalyst bed was analysed. The hydrocarbon concentration was analysed by gas chromatography and the oxygen concentration was analysed using an oxygen meter manufactured by Teledyne Analytical instruments Inc.

EXAMPLE 5

In the above General Experimental Procedure 1, the gas feed was introduced into the reactor containing Catalyst C at 100° C., at which condition the oxygen concentration was 700 ppm. After 29 minutes on stream the temperature was increased to 120° C. and the oxygen concentration fell to 300 ppm. The temperature was then increased to 140° C. after 76 minutes on stream and the oxygen concentration fell to 0.1 ppm. After 116.5 hours on stream the oxygen had risen to 3.1 ppm. The temperature was then increased to 150° C. and the oxygen concentration fell to 0 ppm and remained at 0 ppm until a total of 196 hours on stream when the experiment was terminated. No hydrogenation of acetylene or ethylene was detected under any of these conditions.

EXAMPLE 6

In the above General Experimental Procedure 1, the gas feed was introduced into the reactor containing Catalyst D at 150° C. The oxygen concentration was <0.1 ppm after 16 hours on stream. After 20 hours on stream the temperature was dropped to 120° C. and the oxygen concentration increased to 1.4 ppm. No hydrogenation of acetylene or ethylene was detected under any of these conditions.

EXAMPLE 7

In the above General Experimental Procedure 1, the gas feed was introduced into the reactor containing Catalyst E at 150° C. The oxygen concentration fell to 0 ppm after 6 hours on stream. After 23 hours on stream the temperature was dropped to 120° C. and the oxygen concentration increased to 3 ppm. No hydrogenation of acetylene or ethylene was detected under any of these conditions.

The results from Examples 5 to 7 indicate that the oxygen was removed from the gas mixture without reaction of the olefin.

General Experimental Procedure 2

Prior to commencing General Experimental Procedure 2, the catalyst was optionally reduced. The catalyst was reduced by passing a 1:1 v/v hydrogen:nitrogen mixture at 60 nl/h flow rate over the catalyst, heating to 150° C., maintaining at this temperature for 3 hours, removing the hydrogen component of the mixture and cooling to ambient temperature under nitrogen flow. The reduced catalyst was stored at ambient temperature under 2 barg of nitrogen prior to use in General Experimental Procedure 2.

A sample of catalyst (optionally reduced) was loaded into a stainless steel tubular reactor (10 mm internal diameter) supported downstream by a glass wool plug, with another glass wool plug upstream. Thermocouples were located on top of the glass wool plug upstream of the catalyst, and below the glass wool plug downstream, to measure gas inlet and outlet temperatures. A nitrogen stream was passed over the catalyst to purge the system of air. An initial gas feed was then passed over the catalyst at ambient temperature at the required flow rate. The temperature was then raised using an external furnace to the required value. The composition of the gas exiting the catalyst bed was analysed. The hydrocarbon concentration was analysed by gas chromatography and the oxygen concentration was analysed using an oxygen meter manufactured by Teledyne Analytical Instruments Inc.

EXAMPLE 8

In this Example, Catalyst D was reduced prior to use in General Experimental Procedure 2. The gas feed comprised, by volume, 0.17% oxygen, 39.74% hydrogen, 15.34% ethylene, 3.68% carbon monoxide, 1.72% carbon dioxide, 0.15% acetylene, 0.12% 1,3 butadiene and 39.03% nitrogen. The GHSV was 20,400 $h^{-1}$, catalyst volume 3 and reactor pressure was 2 barg. The amount of oxygen present in the gas exiting from the catalyst bed at various temperatures is given in Table 2. Also shown in Table 2 are the amounts of acetylene, ethylene and 1,3 butadiene remaining in the gas exiting from the catalyst bed expressed as a percentage of the amounts of acetylene, ethylene and 1,3 butadiene present in the initial gas feed respectively.

TABLE 2

| Temp ° C. | Oxygen ppm | % unreacted Acetylene | % unreacted Ethylene | % unreacted 1,3 Butadiene |
|---|---|---|---|---|
| 101 | 1450 | 67 | 100 | 100 |
| 131 | 1150 | 53 | 99.99 | 100 |
| 153 | 620 | 40 | 99.98 | 100 |
| 195 | 2.7 | 13 | 99.92 | 92 |
| 173 | 0.6 | 60 | 99.97 | 83 |

EXAMPLE 9

In this Example, Catalyst D (non-reduced) was used in General Experimental Procedure 2. The gas feed comprised, by volume, 0.13% oxygen, 38.03% hydrogen, 15.89% ethylene, 3.89% carbon monoxide, 1.75% carbon dioxide, 0.14% acetylene, 0.12% 1,3 butadiene and 40.04% nitrogen. The GHSV was 10,200 h$^{-1}$, catalyst volume and reactor pressure was 2 barg. The amount of oxygen present in the gas exiting from the catalyst bed at various temperatures is given in Table 3. Also shown in Table 3 are the amounts of acetylene, ethylene and 1,3 butadiene remaining in the gas exiting from the catalyst bed expressed as a percentage of the amounts of acetylene, ethylene and 1,3 butadiene present in the initial gas feed respectively.

TABLE 3

| Temp ° C. | Oxygen ppm | % unreacted Acetylene | % unreacted Ethylene | % unreacted 1,3 Butadiene |
|---|---|---|---|---|
| 98 | 1150 | 100 | 100 | 100 |
| 130 | 560 | 100 | 100 | 100 |
| 139 | 4 | 100 | 100 | 100 |
| 164 | 2.4 | 64 | 99.43 | 100 |
| 186 | 2.2 | 14 | 99.0 | 83.3 |

EXAMPLE 10

In this Example, Catalyst D (non-reduced) was used in General Experimental Procedure 2. The gas feed comprised, by volume, 0.13% oxygen, 38.19% hydrogen, 16.96% ethylene, 4.03% carbon monoxide, 0.28% carbon dioxide, 0.15% acetylene, 0.12% 1,3 butadiene and 40.15% nitrogen. The GHSV was 10,200 h$^{-1}$ catalyst volume 6 and reactor pressure was 2 barg. The amount of oxygen present in the gas exiting from the catalyst bed at various temperatures is given in Table 4. Also shown in Table 4 are the amounts of acetylene, ethylene and 1,3 butadiene remaining in the gas exiting from the catalyst bed expressed as a percentage of the amounts of acetylene, ethylene and 1,3 butadiene present in the initial gas feed respectively.

TABLE 4

| Temp ° C. | Oxygen ppm | % unreacted Acetylene | % unreacted Ethylene | % unreacted 1,3 Butadiene |
|---|---|---|---|---|
| 100 | 560 | 100 | 100 | 100 |
| 139 | 0.7 | 100 | 100 | 100 |
| 159 | 0.3 | 60 | 100 | 100 |
| 180 | 0.2 | 47 | 100 | 100 |

General Experimental Procedure 3

A 3 ml sample of catalyst was loaded into a stainless steel tubular reactor (10 mm internal diameter) supported downstream by a glass wool plug, with another glass wool plug upstream. Thermocouples were located on top of the glass wool plug upstream of the catalyst, and below the glass wool plug downstream, to measure gas inlet and outlet temperatures. A nitrogen stream was passed over the catalyst to purge the system of air. The catalyst was reduced by passing a 1:1 v/v hydrogen:nitrogen mixture at 60 nl/h flow rate and 2 barg pressure over the catalyst, heating to 175° C., maintaining at this temperature for 4 hours, and cooling to ambient temperature under the hydrogen:nitrogen flow. The reduced catalyst was stored at ambient temperature under 2 barg of nitrogen prior to use.

An initial gas feed was then passed through a water-filled container at 20° C., to saturate the gas with water prior to passing over the catalyst at ambient temperature at the required flow rate. The temperature was then raised using an external furnace to the required value. The composition of the gas exiting the catalyst bed was analysed. The hydrocarbon concentration was analysed by gas chromatography and the oxygen concentration was analysed using an oxygen meter manufactured by Teledyne Analytical Instruments Inc.

COMPARATIVE EXAMPLE 5

Comparative Catalyst F was used in General Experimental Procedure 3. The initial gas feed comprised, by volume, 0.13% oxygen, 31.25% hydrogen, 16.42% ethylene, 11.95% carbon monoxide, 2.6% carbon dioxide, 0.13% acetylene, 0.47% 1,3-butadiene and 37.19% nitrogen. The GHSV was 10,667 h$^{-1}$, and the reactor pressure was 2 barg. The amount of oxygen present in the gas exiting from the catalyst bed at various temperatures is given in Table 5. Also shown in Table 5 are the amounts of acetylene, ethylene and 1,3 butadiene remaining in the gas exiting from the catalyst bed expressed as a percentage of the amounts of acetylene, ethylene and 1,3 butadiene present in the initial gas feed respectively.

TABLE 5

| Temp ° C. | Oxygen ppm | % unreacted Acetylene | % unreacted Ethylene | % unreacted 1,3 Butadiene |
|---|---|---|---|---|
| 120 | 1000 | 73 | 100 | 71 |
| 140 | 955 | 36 | 100 | 89 |
| 160 | 850 | 18 | 98.41 | 71 |
| 183 | 680 | 0 | 88.78 | 23 |

COMPARATIVE EXAMPLE 6

Comparative Catalyst F was used in General Experimental Procedure 3. The initial gas feed comprised, by volume, 0.15% oxygen, 23.81% hydrogen, 16.68% ethylene, 12.14% carbon monoxide, 2.64% carbon dioxide, 0.13% acetylene, 0.47% 1,3-butadiene and 44.1% nitrogen. The GHSV was 10,500 h$^{-1}$, and the reactor pressure was 26.5 barg. The amount of oxygen present in the gas exiting from the catalyst bed at various temperatures is given in Table 6. Also shown in Table 6 are the amounts of acetylene, ethylene and 1,3 butadiene remaining in the gas exiting from the catalyst bed expressed as a percentage of the amounts of acetylene, ethylene and 1,3 butadiene present in the initial gas feed respectively.

TABLE 6

| Temp ° C. | Oxygen ppm | % unreacted Acetylene | % unreacted Ethylene | % unreacted 1,3-Butadiene |
|---|---|---|---|---|
| 120 | 870 | 80 | 100 | 100 |
| 144 | 760 | 53 | 100 | 100 |
| 187 | 350 | 0 | 95.76 | 100 |

EXAMPLE 11

Catalyst G was used in General Experimental Procedure 3. The initial gas feed comprised, by volume, 0.13% oxygen, 25% hydrogen, 18.47% ethylene, 13.45% carbon monoxide, 2.93% carbon dioxide, 0.15% acetylene, 0.52% 1,3-butadiene and 39.5% nitrogen. The GHSV was 10,667 $^{-1}$, and the reactor pressure was 2 barg. The amount of oxygen present in the gas exiting from the catalyst bed at various temperatures is given in Table 7. Also shown in Table 7 are the amounts of acetylene, ethylene and 1,3 butadiene remaining in the gas exiting from the catalyst bed expressed as a percentage of the amounts of acetylene, ethylene and 1,3-butadiene present in the initial gas feed respectively.

TABLE 7

| Temp ° C. | Oxygen ppm | % unreacted Acetylene | % unreacted Ethylene | % unreacted 1,3 Butadiene |
|---|---|---|---|---|
| 121 | 950 | 93 | 100 | 100 |
| 140 | 900 | 79 | 100 | 100 |
| 180 | 660 | 36 | 100 | 98 |
| 190 | 560 | 21 | 100 | 35 |

EXAMPLE 12

Catalyst G was used in General Experimental Procedure 3. The initial gas feed comprised, by volume, 0.13% oxygen, 25% hydrogen, 18.47% ethylene, 13.45% carbon monoxide, 2.93% carbon dioxide, 0.15% acetylene, 0.52% 1,3-butadiene and 39.5% nitrogen. The GHSV was 10,667 h$^{-1}$, and the reactor pressure was 26.5 barg. The amount of oxygen present in the gas exiting from the catalyst bed at various temperatures is given in Table 8. Also shown in Table 8 are the amounts of acetylene, ethylene and 1,3-butadiene remaining in the gas exiting from the catalyst bed expressed as a percentage of the amounts of acetylene, ethylene and 1,3-butadiene present in the initial gas feed respectively.

TABLE 8

| Temp ° C. | Oxygen ppm | % unreacted Acetylene | % unreacted Ethylene | % unreacted 1,3-Butadiene |
|---|---|---|---|---|
| 120 | 640 | 100 | 100 | 100 |
| 140 | 480 | 85 | 100 | 100 |
| 181 | 34 | 15 | 99.24 | 100 |
| 190 | 3.3 | 0 | 97.47 | 100 |

Comparison of results from Example 12 with Comparative Example 6 show the beneficial effect of the presence of tin on the catalyst when the reaction is carried out at elevated pressure (better oxygen removal and less detrimental ethylene hydrogenation). Comparison of results from Example 11 and Example 12 show the benefit of carrying the reaction out at high pressure (better oxygen removal but no significant promotion of the detrimental ethylene hydrogenation reaction)

The invention claimed is:

1. A process for the removal of oxygen from a gas mixture comprising oxygen, at least one olefin, hydrogen, carbon monoxide and optionally at least one alkyne, the ratio of oxygen:hydrogen in the gas mixture being 1 part by volume of oxygen to at least 5 parts by volume of hydrogen, which process comprises contacting the gas mixture with a catalyst in a reaction zone under conditions sufficient to oxidise at least a portion of the hydrogen and to oxidise at least a portion of the carbon monoxide and without significant hydrogenation of the at least one olefin, wherein the catalyst comprises at least one metal or oxide of a metal from the $10^{th}$ group of the Periodic Table of Elements, the metal or oxide of the metal being supported on an oxide support, provided that the catalyst also comprises tin.

2. A process according to clam 1 in which the catalyst comprises at least 0.01 wt %, based on the total weight of the dry catalyst, of at least one metal or oxide of a metal selected from the group consisting of nickel, palladium and platinum supported on silica or alumina.

3. A process according to claim 2 wherein the metal is platinum and is present in an amount in the range 0.01-15 wt % based on the total weight of the dry catalyst and is supported on silica.

4. A process according to claim 2 wherein tin is present in the catalyst in an amount in the range 0.01 to 60 wt % based on the total dry weight of the catalyst.

5. A process according to claim 1 wherein the process comprises the steps:
(a) contacting at least one hydrocarbon with a molecular oxygen-containing gas in a first reaction zone with a catalyst capable of supporting combustion beyond the normal fuel-rich limit of flammability and wherein the stoichiometric ratio of hydrocarbon to oxygen is 5 to 16 times the stoichiometric ratio of hydrocarbon to molecular oxygen-containing gas for complete combustion to carbon dioxide and water, to produce a product stream comprising oxygen, at least one olefin, hydrogen, carbon monoxide and optionally at least one alkyne,
(b) contacting in a second reaction zone, at least a portion of the product stream from step (a) having a ratio of oxygen to hydrogen of at least one part by volume of oxygen to at least 5 parts by volume of hydrogen with a catalyst under conditions sufficient to oxidise at least a portion of the hydrogen and to oxidise at least a portion of the carbon monoxide and without significant hydrogenation of the at least one olefin, wherein the catalyst comprises at least one metal or oxide of a metal from the $10^{th}$ group of the Periodic Table of Elements, the metal or oxide of the metal being supported on an oxide support, provided that the catalyst also comprises tin.

6. A process for the removal of oxygen and alkyne from a gas mixture comprising oxygen, at least one olefin, hydrogen, carbon monoxide and at least one alkyne, the ratio of oxygen:hydrogen in the gas mixture being at least 1 part by volume of oxygen to at least 5 parts by volume of hydrogen, which process comprises contacting the gas mixture with a catalyst in a reaction zone under conditions sufficient to oxidise at least a portion of the hydrogen and to oxidise at least a portion of the carbon monoxide and without significant hydrogenation of the at least one olefin, wherein the catalyst comprises at least one metal or oxide of a metal selected from the group consisting of the $10^{th}$ group and the $11^{th}$ group of the Periodic Table of Elements, the metal or oxide of the metal being supported on an oxide support, provided that where the catalyst comprises at least one metal or oxide of a metal from the $10^{th}$ group of the Periodic Table of Elements supported on an oxide support, the catalyst also comprises tin and provided that where the catalyst comprises at least one metal or oxide of a metal of the $11^{th}$ group of the Periodic Table of Elements the oxide support is a zeolite.

7. A process according to claim 6 wherein the gas mixture contains 2000 ppm or less of oxygen.

8. A process according to claim 6 wherein the gas mixture comprises at least 10 vol % of hydrogen.

9. A process according to claim 8 in which the gas mixture comprises at least 20 vol % hydrogen.

10. A process according to claim 6 in which the gas mixture comprises from greater than 0 up to and including 20 vol % alkyne.

11. A process according to claim 10 in which the alkyne is acetylene.

12. A process according to claim 6 wherein the catalyst comprises at least 0.01 wt %, based on the total weight of the dry catalyst, of at least one metal or oxide of a metal selected from the group consisting of copper, silver and gold, supported on a zeolite support.

13. A process according to claim 12 in which the catalyst comprises copper in an amount in the range of from 1 to 15 wt %.

14. A process according to claim 12 wherein the zeolite is zeolite A or zeolite X.

15. A process according to claim 6 in which the catalyst comprises at least 0.01 wt %, based on the total weight of the dry catalyst, of at least one metal or oxide of a metal selected from the group consisting of nickel, palladium and platinum supported on silica or alumina.

16. A process according to claim 15 wherein the metal is platinum and is present in an amount in the range 0.01-15 wt % based on the total weight of the dry catalyst and is supported on silica.

17. A process according to claim 15 wherein tin is present in the catalyst in an amount in the range 0.01 to 60 wt % based on the total dry weight of the catalyst.

18. A process according to claim 6 wherein the gas mixture is contacted with the catalyst in the reaction zone at a temperature in the range 50-300° C.

19. A process according to claim 6 wherein the gas mixture is contacted with the catalyst in the reaction zone at a total pressure in the range 15-35 bara.

20. A process according to claim 6 wherein the process comprises the steps:
  (a) contacting at least one hydrocarbon with a molecular oxygen-containing gas in a first reaction zone with a catalyst capable of supporting combustion beyond the normal fuel-rich limit of flammability and wherein the stoichiometric ratio of hydrocarbon to oxygen is 5 to 16 times the stoichiometric ratio of hydrocarbon to molecular oxygen-containing gas for complete combustion to carbon dioxide and water, to produce a product stream comprising oxygen, at least one olefin, hydrogen, carbon monoxide and at least one alkyne,
  (b) contacting in a second reaction zone, at least a portion of the product stream from step (a) having a ratio of oxygen to hydrogen of at least one part by volume of oxygen to at least 5 parts by volume of hydrogen with a catalyst under conditions sufficient to oxidise at least a portion of the hydrogen and to oxidise at least a portion of the carbon monoxide and without significant hydrogenation of the at least one olefin, wherein the catalyst comprises at least one metal or oxide of a metal selected from the group consisting of the $10^{th}$ group and the $11^{th}$ group of the Periodic Table of Elements, the metal or oxide of the metal being supported on an oxide support, provided that where the catalyst comprises at least one metal or oxide of a metal from the $10^{th}$ group of the Periodic Table of Elements supported on an oxide support, the catalyst also comprises tin and provided that where the catalyst comprises at least one metal or oxide of a metal of the $11^{th}$ group of the Periodic Table of Elements the oxide support is a zeolite.

* * * * *